United States Patent [19]

Petrosky

[11] Patent Number: 4,922,043

[45] Date of Patent: May 1, 1990

[54] MANUFACTURE OF METHYL CHLORIDE BY HYDROCHLORINATING METHANOL, USING A SPLIT METHANOL FEED

[75] Inventor: Jimmy T. Petrosky, Wichita, Kans.

[73] Assignee: Vulcan Materials Company, Birmingham, Ala.

[21] Appl. No.: 279,093

[22] Filed: Dec. 2, 1988

[51] Int. Cl.$^5$ ............................................. C07C 17/16
[52] U.S. Cl. .................................................. 570/258
[58] Field of Search ............................. 570/258, 259

[56] References Cited

U.S. PATENT DOCUMENTS

| | | |
|---|---|---|
| 2,026,131 | 12/1935 | Klein et al. . |
| 2,091,986 | 9/1937 | Holt et al. . |
| 2,421,441 | 6/1947 | Thronson et al. . |
| 2,847,484 | 8/1958 | Kolker . |
| 3,981,938 | 9/1976 | Steele et al. . |

FOREIGN PATENT DOCUMENTS

| | | |
|---|---|---|
| 2447551 | 4/1975 | Fed. Rep. of Germany . |
| 1560892 | 2/1980 | United Kingdom . |

OTHER PUBLICATIONS

"Kirk–Othmer Encyclopedia of Chemical Technology", vol. 3, p. 741, (1949).

Vulcan Materials Company, "Manufacture of Chloromethanes from Methyl Alcohol and Chlorine".

Sconce, "Chlorine, Its Manufacture, Properties and Uses", ACS Monograph No. 154, pp. 363–364, and FIG. 12–6 on p. 365.

Encyclopedia of Chemical Processing and Design, vol. 8, pp. 256–259 (1979).

Vulcan Materials Company In–House literature searches dated Jun. 17, 1982; Jan. 7, 1987; and Jul. 23, 1987.

*Primary Examiner*—Howard T. Mars

[57] ABSTRACT

In a process for making methyl chloride by the catalytic hydrochlorination of methanol in the liquid phase, the common formation of unwanted dimethyl ether by-product is reduced by conducting the process in at least two reactors operating in series and by introducing all or substantially all of the required hydrogen chloride feed into the first reactor while splitting the introduction of methanol feed, preferably as a vapor, between or among the reactors.

The overall feed ratio of methanol to hydrogen chloride is in the range between about 0.65 to about 1.0 mol methanol per mol hydrogen chloride. Aqueous zinc chloride is the preferred catalyst.

5 Claims, 1 Drawing Sheet

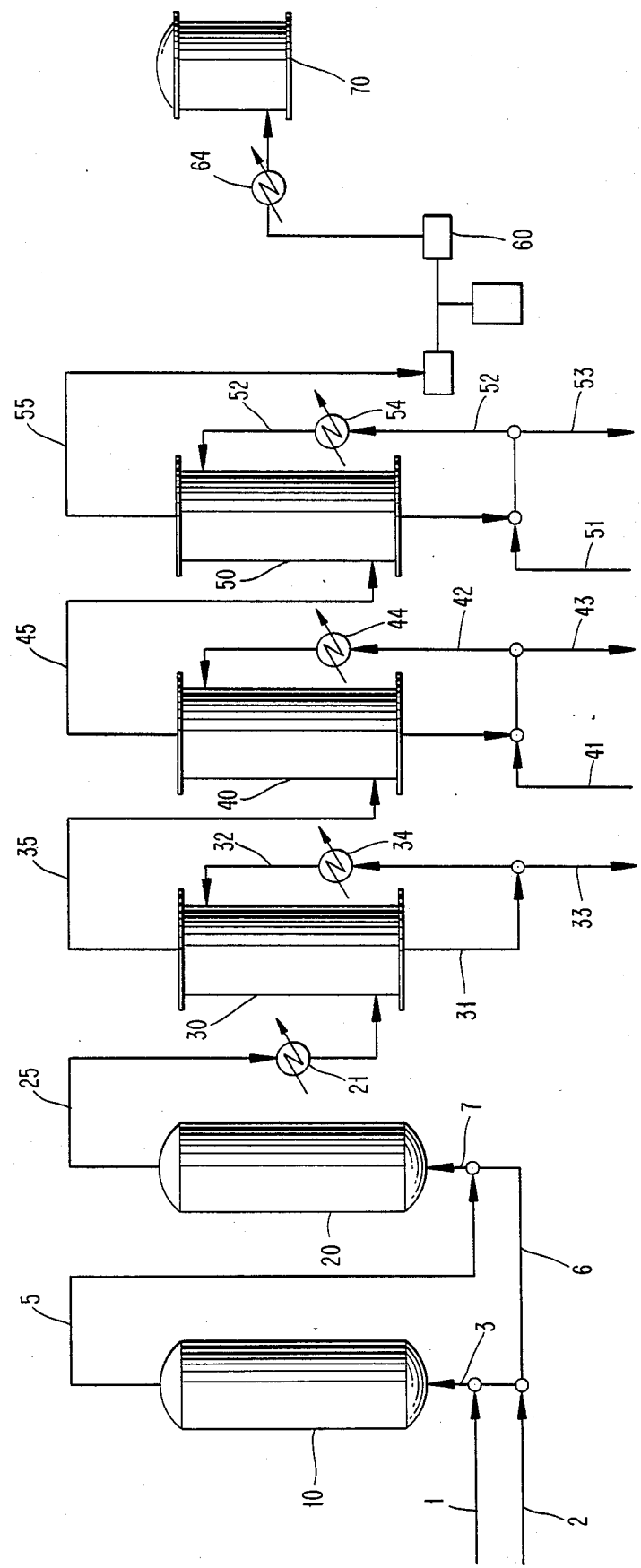

4,922,043

MANUFACTURE OF METHYL CHLORIDE BY HYDROCHLORINATING METHANOL, USING A SPLIT METHANOL FEED

BACKGROUND OF THE INVENTION

1. Field of the Invention

This invention relates to an improved process for making methyl chloride by reacting methanol with hydrogen chloride in the presence of a metal chloride catalyst, e.g., zinc chloride. As such a process normally results in the formation of substantial amounts of dimethyl ether (DME) as an unwanted by-product, the improvement is particularly concerned with a method of reducing such ether formation. 2. Description of the Prior Art Methyl chloride has many uses in industry and science. For instance, it not only finds wide use as a solvent, extractant, propellant or refrigerant, it is also used as a methylating agent in organic synthesis and, importantly, as a starting material in the production of dichloromethane, trichloromethane and carbon tetrachloride by reaction with chloride. Another important use of methyl chloride is as an intermediate in the production of silicones.

A common and economical process for providing methyl chloride involves the hydrochlorination of methanol according to the reaction $MeOH + HCl \rightarrow MeCl + H_2O$. As it is described, for instance, in the Encyclopedia of Chemical Processing and Design, Vol. 8, pp 256-9 (1979), this reaction can be carried out using either a liquid or a solid catalyst. However, the object of this invention is concerned only with the reaction when it is conducted in the liquid phase.

The liquid-phase reaction system is usually conducted in an aqueous medium, at or near atmospheric pressure and at a reaction temperature of from about 100° to about 200° C. Catalysts for the liquid-phase reaction are water solutions of metal chlorides, such as ferric chloride or bismuth oxychloride or most preferably zinc chloride. The reaction has been most commonly carried out by bubbling HCl and methanol as a gaseous mixture through a single reactor or several reactors operating in parallel, although sometimes the reactors have been operated in series. In all such conventional cases, however, substantially all of the methanol and all of the HCl is fed through a single-feed system into the first and in some cases the only reaction stage. As shown in U.S. Patent 2,847,484, when more than one reactor is used, the effluent vapors are passed from the first reactor through a subsequent reactor or reactors operating in series. The temperature of the solution and the concentration of catalyst are so maintained that the water of reaction is continuously vaporized from the reaction mixture along with the methyl chloride, thereby providing continuous operation. By-product hydrogen chloride, such as that available from the chlorination of methane or ethane, can be used.

As the desired methanol hydrochlorination reaction is generally accompanied by a side reaction wherein dimethyl ether (DME) is formed from methanol according to the equation $2MeOH \rightarrow DME + H_2O$, the crude methyl chloride obtained by the hydrochlorination of methanol contains not only water, unreacted methanol, and hydrochloric acid but also a substantial proportion of DME as an impurity. The methanol and hydrochloric acid are usually removed by scrubbing the crude methyl chloride vapor with cold water and then with cold dilute sodium hydroxide solution, and the water and DME are removed by scrubbing with cold concentrated sulfuric acid. The resulting pure methyl chloride vapor is compressed, condensed with cold water, and placed in storage tanks.

While removal of DME from the methyl chloride is readily accomplished by scrubbing with sulfuric acid, not only is its formation wasteful in terms of greater raw material costs, but the disposal of unwanted sulfuric acid-containing DME presents a problem in view of increasing ecological concerns and resulting restriction on the disposal of industrial waste streams.

SUMMARY AND OBJECTS OF THE INVENTION

According to the present invention, when the hydrochlorination reaction is carried out in two or more reactors in series, an improvement in performance is obtained by splitting the methanol feed such that only part of the methanol feed is introduced into the first reactor together with the gaseous hydrogen chloride feed while the effluent from the first reactor is fed into the subsequent reactor or reactors together with the balance of the methanol and with no or only a small amount of additional hydrogen chloride.

While this novel split-feed arrangement was initially tried in the expectation that it would increase the conversion of methanol to methyl chloride, surprisingly, no such increase was found to occur. On the contrary, the conversion of methanol to methyl chloride remained substantially unchanged and the total methanol conversion decreased. However, this seeming disadvantage was more than offset by an entirely unexpected and highly desirable decrease in the conversion of methanol to DME, resulting in a little more unreacted methanol in the reactor effluent but significantly less DME. Of course, unreacted methanol can easily be recovered from the effluent and recycled to the reactors.

Accordingly, it is an object of this invention to reduce raw material costs in the manufacture of methyl chloride by hydrochlorination of methanol.

It is another object to reduce the production of ecologically objectionable by-products, notably DME, in the manufacture of methyl chloride from methanol.

It is further object to provide an improved process for making methyl chloride from methanol in a series of at least two reaction stages, such that the production of DME is reduced and the amount of sulfuric acid required as a scrubbing liquid in the process is thereby also reduced.

These and other objects, as well as the nature and scope of the invention, and of the manner and process of using it, including the best mode thereof, are more fully described in and will become apparent from the following specification and claims.

It is to be understood that all parts, concentrations, percentages, and proportions of materials are expressed throughout on a weight basis unless otherwise indicated.

DESCRIPTION OF THE DRAWINGS

The drawing is a schematic flow diagram for a process of the invention, comprising two hydrochlorination reactors in series followed by a plurality of scrubbing towers wherein the crude methyl chloride vapor produced in the reactors is purified prior to recovery.

DETAILED DESCRIPTION OF THE INVENTION

In practicing this invention, methyl chloride (b.p. −23.7° C.) is prepared in a continuous process by heating methanol (b.p. 64.5° C.) and hydrogen chloride as a vapor mixture in contact with a hydrochlorination catalyst, e.g., an aqueous solution of ferric chloride, bismuth oxychloride or, most preferably, zinc chloride. The water of reaction is removed from the reaction zone together with the methyl chloride product, by-products such as dimethyl ether (b.p. −24.5° C.), and some unconverted methanol and hydrogen chloride.

Predetermined amounts of methanol and hydrogen chloride are fed to the process preferably, though not necessarily, as substantially anhydrous vapors in an overall ratio in the range between about 0.65 and about 1.0, preferably between about 0.75 and 0.95 mol methanol per mol HCl, with all or substantially all of the hydrogen chloride being fed into a first reactor while the methanol feed is split between consecutive reactors operating in series.

The aqueous catalyst solution desirably contains zinc chloride in a concentration from about 45 to 85 percent, preferably about 65 to 75 percent.

The methanol and HCl are reacted together in the presence of the hydrochlorination catalyst at a temperature in the range between about 100° and about 200° C., preferably between about 135° C. and 190° C., with a pressure in the range between about 1 and about 5 atmospheres, preferably between about 1 and 3 atmospheres.

In the prior art this hydrochlorination reaction has commonly been carried out in a single reaction stage or in a plurality of such reaction stages connected in parallel or in series, but in each such case all of the methanol and HCl are fed into the first reaction stage in substantially or nearly an equimolar amount or with a molar excess of HCl. Often these reactions have been operated with 0-15% excess HCl (an HCl/methanol ratio of 1.00 to 1.15). By contrast, it is the essence of the present invention that the hydrochlorination reaction is carried out in a plurality of successive reaction stages such that all or substantially all the HCl is introduced into the first stage whereas not more than 95 percent, and preferably between 30 and 90 percent, and most preferably only between 40 and 80 percent of the total normal targeted amount of methanol feed required to maintain the preselected overall methanol-to-HCl molar ratio for the system is introduced into the first reaction stage while the balance of the methanol is introduced into the second reaction stage or is split in any suitable proportions between or among several further reaction stages.

For instance, when such a process uses three consecutive reactors, 30 to 40 percent of the total methanol feed may be introduced into the first reactor and the remaining 60 to 70 percent may be split among the other two reactors either in substantially equal or in different proportions, but all or substantially all of the hydrogen chloride is introduced only into the first reactor. The effluent from the first reactor, which in such a case of course contains a substantial proportion of unconverted HCl, is then introduced into the second reactor where the unconverted HCl reacts with the methanol introduced into this reactor, and the effluent from this reactor then continues to the third reactor where the remaining unconverted HCl reacts with the methanol feed introduced into it, and so on.

In other words, it is characteristic of the improved methanol hydrochlorination process of this invention that it is carried out in a series of at least two reactors, or in a pair of such series reactors connected in parallel, such that the mol ratio of MeOH/HCl in the first reaction stage is at least about 0.05 MeOH/1.5 HCl and up to about 0.95 MeOH/1.0 HCl, preferably at least about 0.55 MeOH/1.5 HCl and up to about 0.9 MeOH/1.05 HCl, and the MeOH/HCl mol ratio in the second or subsequent reaction stage or stages is at least up to about 0.95 MeOH/0.95 HCl, preferably at least about 0.1 MeOH/0.6HCl and up to about 0.45 MeOH/0.50 HCl. For instance, in a two-reactor system operated in series with an overall methanol-to-HCl ratio of 1.0/1.1, it is suitable to split the methanol feed between the two reactor stages such that the MeOH/HCl mol ratio is between about 0.95/1.1 and 0.05/1.1 in the first reactor and between about 0.05/0.15 and 0.95/1.05 in the second reactor, it being understood that the portion of the originally fed HCl which remains unreacted in the first stage is then introduced into the second stage as part of the first-stage effluent.

Referring to the drawing, and by way of illustration, a representative embodiment of the invention may be carried out as follows.

Reactors 10 and 20 are reaction vessels substantially filled with an aqueous solution containing about 68 percent zinc chloride. Reactors 10 and 20 are maintained at a temperature of about 150° C. and a pressure of about 30 psig. Anhydrous hydrogen chloride (line 1) and methanol vapor (line 2) are mixed and introduced into a bottom portion of reactor 10, preferably through a perforated sparger tube (not shown). For instance, about 110 pounds mols per hour of HCl and about 80 pound mols per hour of MeOH may thus be fed into the reactor 10 and reacted there upon upward passage through the liquid catalyst phase. The crude vapor effluent, which contains methyl chloride, unreacted hydrogen chloride and methanol, as well as some DME and water, is withdrawn from reactor 10 via line 5, mixed with about 20 pound mols per hour of additional methanol which is introduced via line 6, and introduced to a bottom portion of the second reactor 20, where this additional methanol is reacted with the HCl introduced as part of the reaction mixture withdrawn from reactor 10 via line 5.

Reactor 20 contains aqueous zinc chloride solution in about the same amount and concentration as reactor 10 and is usually maintained under essentially the same conditions of temperatures and pressure as reactor 10.

The vaporous reaction mixture containing crude methyl chloride formed in reactor 20 is withdrawn from an upper portion thereof via line 25 and is then purified in an otherwise conventional manner. For instance, as described in U.S. Patent 2,421,441, the crude methyl chloride product withdrawn from reactor 20 via line 25 may be consecutively treated in a quench tower 30, a caustic scrubber 40 and a sulfuric acid scrubber 50 before the purified methyl chloride is finally liquified for storage by compression and cooling.

Thus, the aqueous scrubbing liquid circulated through tower 30 via lines 31 and 32 is suitably cooled to a temperature preferably not in excess of 40° C., e.g., 20° to 35° C., by passing through a heat exchanger 34, cooling the incoming crude methyl chloride vapor and condensing the water of reaction produced in the process, such excess water being removed in the form of a weak hydrochloric acid solution via line 33 for appropriate further treatment. As the crude methyl chloride withdrawn from reactor 25 has a temperature of about 150° C. it is preferably cooled to between 50° and 60° C. by passing through heat exchanger 21 before it is introduced into water scrubber 30, although this is not essential. By first cooling the crude product stream, a considerable proportion of hydrochloric acid will be condensed from the gaseous product. Good operation is obtained if the water entering the scrubber has a temperature between 10° and 20° C. when the methyl chloride vapor entering the scrubber has a temperature of about 50° C. If the methyl chloride entering the scrubber has a higher temperature, the water entering the scrubber should be adjusted in volume and temperature so that the water leaving the scrubber will preferably not be hotter than about 40° C. To avoid undesirable solubility losses of methyl chloride in the scrubbing liquid, the temperature of the water leaving the quench tower 30 is preferably maintained between about 30° and 40° C.

After scrubbing in tower 30, the vapor is passed via line 35 to a caustic scrubber 40. The dilute caustic solution circulated through scrubber 40 may contain, for instance, about 7 to 10 percent sodium hydroxide and is desirably cooled by passing through heat exchanger 44 to a temperature between about 10° and 25° C., spent caustic solution being withdrawn from the system via line 43 while make-up caustic solution is introduced via line 41. The sodium hydroxide solution circulating in scrubber 40 preferably has a concentration not in excess of 10 percent. If desired, two or more alkali scrubbers can be used in series with successively stronger concentrations. Preferably, the sodium hydroxide solution should contain at least 3 percent sodium hydroxide, and the alkali scrubbers should be operated preferably at temperatures not exceeding 25° C., as higher temperatures can cause some hydrolysis of the methyl chloride.

The vapor scrubbed in tower 40 is finally passed to a drying tower 50 where it is scrubbed with concentrated sulfuric acid, e.g., sulfuric acid the strength of which is at least 60° Be (78% $H_2SO_4$). Referring to the drawing, fresh treating acid is introduced via line 51 while spent acid is withdrawn via line 53, and a heat exchanger 54 is used to cool the circulating acid. The acid serves to purify the product vapor by removing from it both water and organic by-products, notably DME. Finally, the purified product vapor is compressed by means of compressors 60, liquified by passing through heat exchanger 64 and stored in tank 70.

The scrubbers are usually filled with a suitable packing material such as Raschig rings and all process units, including both the reactors and the scrubbers, are of course constructed of suitable corrosion-resistant materials, as is otherwise well known.

EXAMPLES

To illustrate the effectiveness and advantages of the invention, three comparative test runs were conducted. In all these runs, a single laboratory reactor was used. This reactor consisted of an electrically heated and insulated glass pipe 36 inches (91.4 cm) long having a 2-inch (5.08 cm) internal diameter. The reactor was set up in an upright position and closed off at both ends with Teflon polytetrafluoroethylene flanges and was equipped with one mixed-feed inlet line passing into the bottom portion of the reactor and a vapor exit line at the upper end.

In all of the tests, the above described laboratory reactor was used to simulate two reactors operating in series. To do this, in simulating the operation of the first-stage reactor the methanol and HCl vapors were fed into the reactor through a mixed-feed line extending into the bottom portion of the reactor, where the vapors became mixed in the catalyst solution and rose upwardly through it. The reactor contents were maintained at 150° C. and 30 psig pressure as the gaseous reactants bubbled upwardly through the liquid-phase catalyst solution and reacted. The effluent from the reactor was recovered and analyzed. A gas mixture having the same composition as the effluent from the first-stage reactor, either by itself or mixed with an appropriate amount of additional methanol, was then fed as a vapor to the same reactor to simulate the operation of the second-stage reactor operating in series with the first stage reactor. Again the reactor contents were maintained at 150° C. and 30 psig pressure. The effluent from the simulation of the second stage reactor was recovered and analyzed to determine overall two-reactor system performance and efficiencies.

RUN 1. Prior Art: 100% methanol to first reactor, 0% to second reactor

To the glass reactor already described above, 1941 grams of aqueous solution containing 1281 grams zinc chloride as catalyst was charged, producing a static column of catalyst solution 30 inches (76 cm) deep. In simulating a first reaction stage, 12.1 gram moles per hour of vaporized methanol and 13.3 gram moles per hour of anhydrous HCl gas were fed to this system as a mixed feed, the effluent was analyzed, and then, simulating a second reaction stage, a gas mixture having the same composition as the effluent from the first-stage reactor was fed to the same system (without any additional methanol). The following overall performance conversions were obtained:

| | |
|---|---|
| Carbon to Methyl Chloride | 98.12% |
| Carbon to DME | 1.40% |
| Total Carbon | 99.52% |
| HCl | 91.82% |
| Unconverted Methanol | 0.48% |

RUN 2. Split methanol: 90% to first reactor, 10% to second reactor

As in Run 1, about 13.3 gram mols per hour of anhydrous HCl gas were fed to the reactor serving as a first stage. However, to exemplify the present invention, only 90% or 10.9 gram mols per hour of vaporized methanol was fed to this first stage. The remaining 1.2 gram mols per hour of vaporized methanol were added to a gas feed mixture having the same composition as the vapor effluent mixture from the first reaction stage and such mixed feed was then fed into the reactor in simulation of two reactors operating in series. The catalyst charge and the reactor temperatures and pressures were the same as in Run 1. The following overall performance conversion were obtained:

| | |
|---|---|
| Carbon to Methyl Chloride | 97.88% |
| Carbon to DME | 0.81% |
| Total Carbon | 98.68% |
| HCl | 92.68% |

-continued

| Unconverted Carbon | 1.32% |
|---|---|

It can be seen that the conversion to unwanted DME in Run 2 is 42.9% less than in Run 1.

RUN 3. Split methanol: 75% to the first reactor, 25% to the second reactor

As in Run 1 and Run 2, 13.3 gram mols per hour of anhydrous HCl gas was fed to the reactor in a first stage. To further exemplify the present invention, only 75% or 9.08 gram mols per hour of vaporized methanol was fed to the reactor in this first stage. The remaining 3.03 gram mols per hour of vaporized methanol and a gas feed mixture having the same composition as the vapor effluent from the first stage were then fed together into the reactor serving as a second reaction stage. The catalyst charge and the reactor temperatures and pressures were the same as in Runs 1 and 2. The following overall performance conversions were obtained:

| Carbon to Methyl Chloride | 97.82% |
|---|---|
| Carbon to DME | 0.53% |
| Total Carbon | 98.35% |
| HCl | 91.73% |
| Unconverted Methanol | 1.65% |

The conversion to DME in Run 3 represents a 62.1% reduction in DME production versus Run 1.

For a better overview, the data referred to in Runs 1, 2 and 3 are presented in Table I below.

TABLE I
LIQUID-PHASE HYDROCHLORINATION OF METHANOL
STAGED METHANOL ADDITION RUNS
Zinc Chloride Catalyst, 30 psig Pressure
150° C. Temperature, 30-inch Bed Height

| Run Number | 1 | 2 | 3 |
|---|---|---|---|
| Stage 1 Feeds Gram Mols/Hr | | | |
| CH$_3$OH | 12.11 | 10.90 | 9.08 |
| HCl | 13.32 | 13.32 | 13.32 |
| Stage 2 Feed Gram Mols/Hr | | | |
| Additional CH$_3$OH | 0 | 1.20 | 3.03 |
| % of Total Methanol Feed to | | | |
| Stage 1 | 100 | 90 | 75 |
| Stage 2 | 0 | 10 | 25 |
| Overall Performance Conversion, % | | | |
| Carbon to CH$_3$Cl | 98.12 | 97.88 | 97.82 |
| Carbon to DME | 1.40 | .81 | .53 |
| Total Carbon | 99.52 | 98.68 | 98.35 |
| HCl | 91.82 | 92.68 | 91.73 |

It can be seen from these data that splitting the methanol feed between consecutive stages of a process for making methyl chloride by hydrochlorination of methanol results in a very substantial reduction in the production of unwanted DME. While the total conversion of methanol is also reduced somewhat when the methanol feed is split between consecutive reaction stages, the unreacted methanol can easily be recovered from the crude reaction product and recycled to the process as feed to the first reaction stage or to any subsequent reaction stage.

It should be noted that while in the described embodiments the methanol feed was split between only two reaction stages, the process can of course be similarly conducted using a greater number of reaction stages in series, e.g., anywhere from 3 to 5 or more stages, and the methanol feed can in such a case be suitably split among all such stages. The total number of stages utilized depends primarily on the economics of the additional capital required versus the improved efficiencies obtained by additional reactors. Instead of carrying out the hydrochlorination reaction in a series of separate reactors, it may be similarly carried out in a column containing a suitable solid packing as well as the liquid phase catalyst, in which case the hydrogen chloride gas and some of the methanol are introduced at the bottom and suitable additional amounts of methanol are then introduced at various consecutively higher levels of the column.

Although the invention has been described with preferred embodiments, it is to be understood that variations and modifications may be employed without departing from the scope or spirit of this invention, as will be apparent to those skilled in the art. Such variations and modifications are to be considered within the scope of the appended claims.

What is claimed is:

1. In a process for making methyl chloride by reacting methanol and hydrogen chloride in aqueous liquid phase in the presence of a catalyst in a reaction system comprising at least two reaction stages in series, said methanol and hydrogen chloride being introduced into the process in total amounts corresponding to an overall ratio of between about 0.65 and 1.0 mol of methanol per mol of hydrogen chloride, the improvement which comprises (a) introducing from about 5 to about 95 percent of the total amount of methanol and substantially all of the hydrogen chloride into a first reaction stage containing a metal chloride catalyst in a first aqueous liquid phase, and intimately contacting said introduced methanol and hydrogen chloride with said first liquid phase, thereby producing methyl chloride, dimethyl ether and water, (b) withdrawing from said first reaction stage a first product vapor stream comprising unreacted hydrogen chloride and substantially all the water, dimethyl ether and methyl chloride produced in said first reaction stage and introducing said vapor stream into at least one successive reaction stage containing a metal chloride catalyst in a second aqueous liquid phase, also introducing the balance of the total amount of methanol into said at least one successive reaction stage, and intimately contacting said first product vapor stream and said additional methanol with said second liquid phase, (c) withdrawing from the last of said series of successive reaction stages a second product vapor stream comprising methyl chloride admixed with hydrogen chloride, dimethyl ether and water vapor, and (d) separating and recovering methyl chloride from said withdrawn product vapor stream.

2. A process according to claim 1 wherein the reaction system comprises two consecutive reaction stages wherein from 30 to 90 percent of the total amount of methanol is fed into the first of said reaction stages and from 10 to 70 percent of the total amount of methanol is fed into the second of said reaction stages.

3. A process according to claim 1 which comprises more than two reaction stages operating in series and wherein a product vapor stream is withdrawn from each but the last reaction stage and fed into the next consecutive reaction stage, and the product vapor stream withdrawn from the last reaction stage is recovered and methyl chloride is separated therefrom.

4. A process according to claim 1 in which the catalyst-containing liquid phases are maintained at temperatures in the range between 135° and 190° C.

5. In a process for making methyl chloride by reacting methanol and hydrogen chloride in aqueous liquid phase at a reaction temperature in the range between 135° and 190° C. in the presence of a hydrochlorination catalyst in a reaction system comprising two reaction stages in series, said methanol and hydrogen chloride being introduced into the process in total amounts corresponding to an overall ratio of between about 0.65 and 1.0 mol of methanol per mol of hydrogen chloride, the improvement which comprises (a) introducing from about 10 to about 90 percent of the total amount of methanol and substantially all of the hydrogen chloride as vapors into a first reaction stage containing a first aqueous liquid solution comprising 45 to 85 weight percent zinc chloride, and intimately contacting said introduced methanol and hydrogen chloride vapors with said first liquid phase, thereby producing methyl chloride, dimethyl ether and water, (b) withdrawing from said first reaction stage a first product vapor stream comprising unreacted hydrogen chloride and substantially all the water, dimethyl ether and methyl chloride produced in said first reaction stage and introducing said vapor stream into a second reaction stage containing a second aqueous liquid solution comprising 45 to 85 weigh percent zinc chloride, also introducing the balance of the methanol as a vapor into said second reaction stage, and intimately contacting said first product vapor stream and said additional methanol with said second aqueous liquid solution, (c) withdrawing from said second reaction stage a second product vapor stream comprising methyl chloride admixed with hydrogen chloride, dimethyl ether and water vapor, (d) consecutively scrubbing said withdrawn second product stream with liquid water, an aqueous caustic solution and a concentrated sulfuric acid solution, and (e) recovering methyl chloride therefrom.

* * * * *